United States Patent [19]

Vienamo et al.

[11] Patent Number: 5,410,757
[45] Date of Patent: May 2, 1995

[54] FACE SHIELD

[75] Inventors: Teppo T. Vienamo, Helsinki; Pauli J. Saari, Isokyrö ; Timo E. Holmlund; Jyrki H. V. Jäarvinen, both of Vassa, all of Finland

[73] Assignee: Kemira Oy, Finland

[21] Appl. No.: 247,495

[22] Filed: May 23, 1994

Related U.S. Application Data

[63] Continuation of Ser. No. 829,758, Jan. 31, 1992, abandoned.

[30] Foreign Application Priority Data

Jun. 1, 1990 [FI] Finland .................................. 902746

[51] Int. Cl.6 ............................................ A41D 13/00
[52] U.S. Cl. ........................ 2/9; 128/201.23; 2/171.3
[58] Field of Search ................. 2/8, 424, 11, 426, 436, 2/437, 9, 171.3, 173, 206; 128/201.22, 201.23, 201.24, 201.25

[56] References Cited

U.S. PATENT DOCUMENTS

| | | | |
|---|---|---|---|
| 2,099,464 | 11/1937 | Bruner et al. | |
| 2,156,852 | 5/1939 | Horak | 2/424 |
| 2,619,644 | 12/1952 | Christensen et al. | 2/436 |
| 3,137,295 | 6/1964 | Stansfield | 2/8 |
| 3,649,964 | 3/1972 | Schoelz et al. | |
| 4,011,595 | 3/1977 | Shields | 2/436 |
| 4,528,701 | 7/1985 | Smith | 2/438 |
| 4,534,344 | 8/1985 | Constance-Hughes | 128/201.23 |
| 4,676,236 | 6/1987 | Piorkowski et al. | 128/201.23 |
| 4,890,335 | 1/1990 | Crowson . | |
| 5,009,225 | 4/1991 | Vrabel | 128/201.24 |

FOREIGN PATENT DOCUMENTS

| | | | |
|---|---|---|---|
| 457339 | 6/1949 | Canada | 2/436 |
| 815402 | 7/1937 | France . | |
| 1265342 | 4/1968 | Germany . | |
| 2932348 | 2/1981 | Germany . | |
| 354416 | 3/1973 | Sweden . | |
| 455158 | 6/1988 | Sweden . | |
| 2203050 | 10/1988 | United Kingdom . | |

Primary Examiner—Clifford D. Crowder
Assistant Examiner—Michael A. Neas
Attorney, Agent, or Firm—Willian Brinks Hofer Gilson & Lione

[57] ABSTRACT

A face shield comprising a frame (1), a glass (2) attached to the frame, a padding (3) between the frame and the face and an attaching portion, for example, a ribbon (4) encircling the head, and to which face shield air is led. The frame is hollow so that the air led into the face shield is directed into the hollow frame and the frame comprises openings through which the air is discharged inside the face shield.

15 Claims, 3 Drawing Sheets

FACE SHIELD

CROSS-REFERENCE TO RELATED APPLICATION

This application is a continuation of application Ser. No. 07/829,758, filed Jan. 31, 1992, now abandoned, which is a continuation of International application PCT/FI91/00174, filed May 31, 1991, which designated the United States of America.

BACKGROUND OF THE INVENTION

The present invention relates to a face shield comprising a frame, a glass attached to the frame, a padding between the frame and the face and an attachment portion, like a ribbon encircling the head, and into which face shield air is led.

As is commonly known, so called whole face masks of the type made of rubber, comprising regulating valves and fastened by ribbons, hurt and are heavy as well as expensive to make. Because of the weight, these face masks usually require 4 to 5 buckles, whereby they are difficult to put on. Specifically, welding masks, into which air is led through canals, are often very heavy and the portions encircling the head are usually made of hard plastic. The big dimensions complicate use and edge sealing is difficult to accomplish. So called hoods made of, for example, plastic cloth, paper or plastic are reasonably priced, but difficult to use and in case of an accident they may lead to risk of suffocation.

SUMMARY OF THE INVENTION

The aim of the invention is to achieve a new type of face shield which is easy to use as well as light. The face shield according to the invention is characterized by the frame being hollow so that the air directed to the face shield is directed to the hollow frame, and the frame comprises openings through which the air is discharged into the face shield. Said face shield is intended for use with a blowing device or compressed air. The hollow frame made of light and flexible plastic yields according to the shape of the face and is of such size that the mouth, nose and eyes will stay inside the frame. Because the shield is blow moulded, the cheapest plastic qualities may be used as raw materials and, in addition, all essential parts are formed in one stage of operation. The face shield comprises a few parts which makes it reasonably priced and light. Due to the form and lightness of the construction it is possible to use a fastening ribbon known from sports glasses, which ribbon is easier to handle than the previously used groups of ribbons comprising two or more ribbons.

By placing press buttons or other suitable fastening means in the frame it is possible to attach an additional shield made of textile, plastic or paper for covering the surface of the head remaining outside the frame. Due to the new structure of the face shield the dimensions of it are such that a hardhat, hearing protectors or even a welding mask may easily be used simultaneously with it. There is also room for spectacles inside the face shield.

One embodiment of the invention is characterized in that the openings are elongated slots located at the sides of the frame and are directed towards the glass so that the air is discharged in front of the face to be breathed and simultaneously to blow away possible mist from the inner surface of the glass. Thus enough air is achieved for both breathing and removing mist even when the wearer of the face shield breathes heavily or speaks.

Another embodiment of the invention is characterized in that the padding between the frame and the face consists of a foam plastic with open cells so that the air, which has been led in to be breathed can together with the exhalation air exit through said padding from inside the face shield. Overpressure is constantly kept up in the face shield so that there is a continuous air flow through the padding. The padding portion can be manufactured in such a way that it can be easily changed in order to maintain hygienic demands. It can, for example, contain a tape attachment. The replaceable paddings may be of different size and thickness whereby the best fitness is achieved for faces of different sizes.

BRIEF DESCRIPTION OF THE DRAWINGS

The invention will be described in the following with reference to the enclosed drawings, in which.

DETAILED DESCRIPTION OF THE PRESENTLY PREFERRED EMBODIMENT

Figure 1:
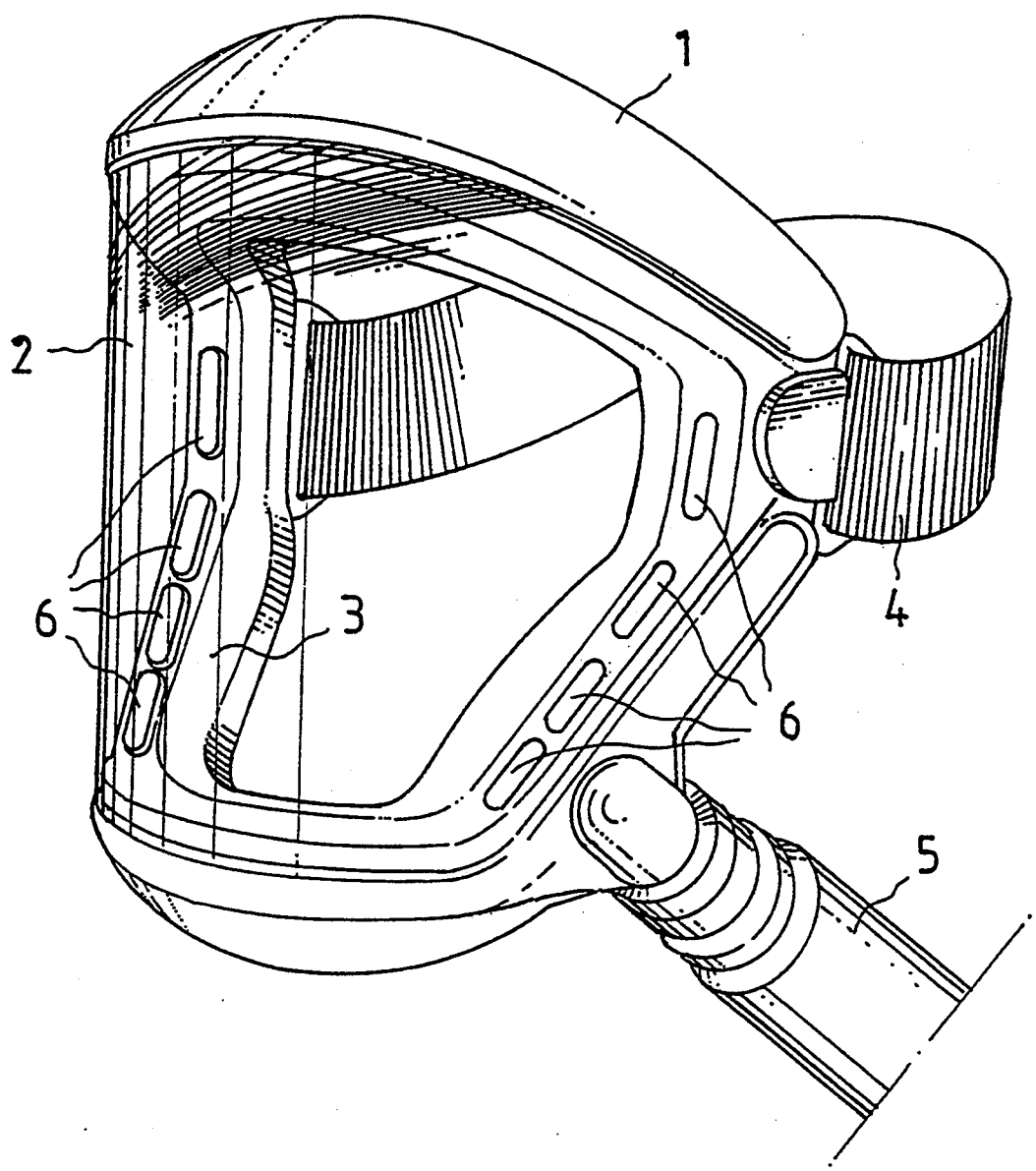
FIG. 1 is a diagonal front view of the face shield.
Figure 2:
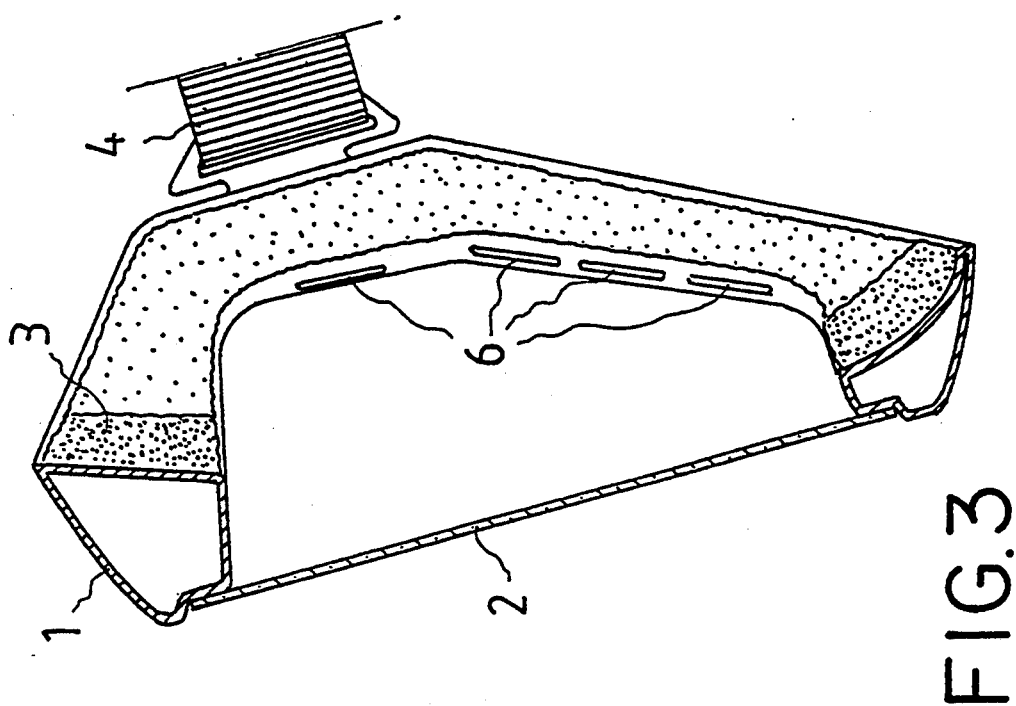
FIG. 2 is a side view of the face shield.
Figure 3:
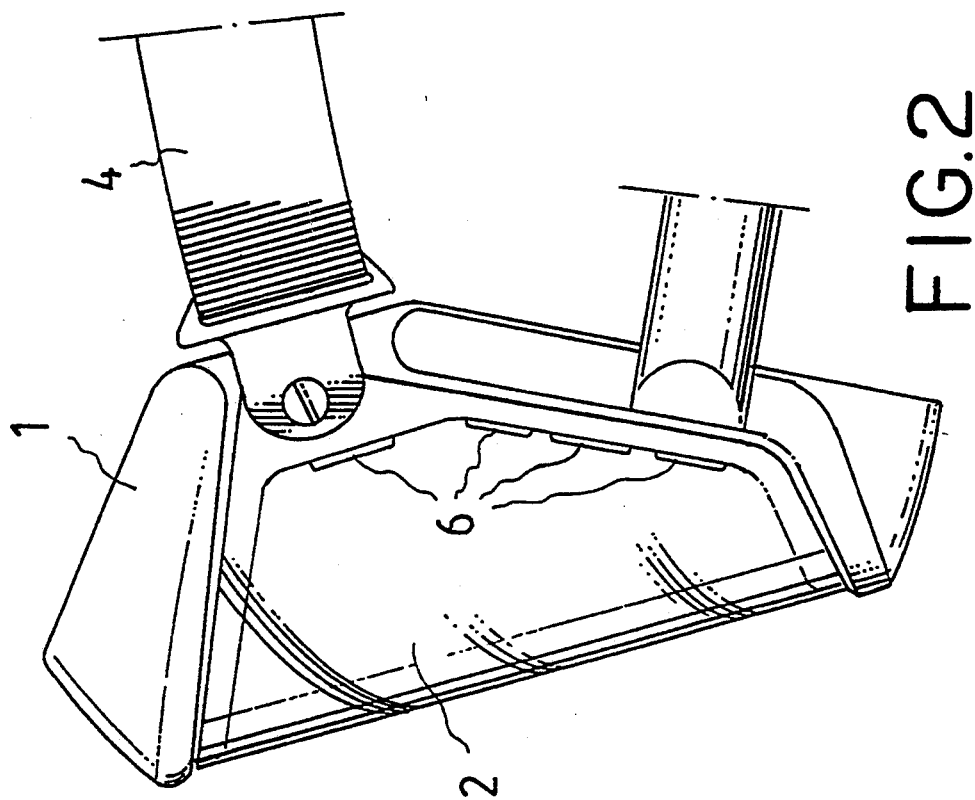
FIG. 3 is a sectional view of the face shield.
Figure 4:
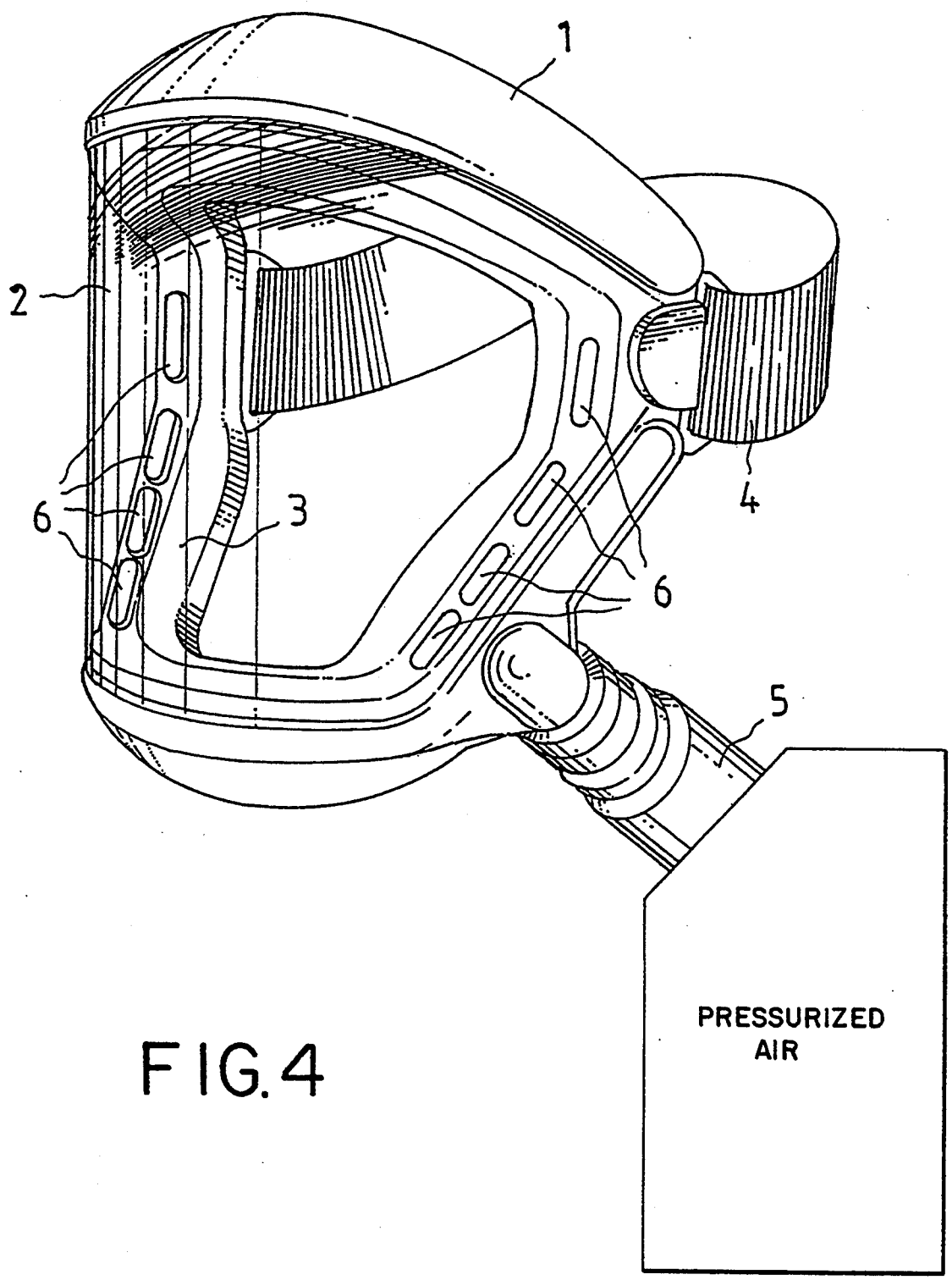
FIG. 4 is a diagonal front view of the face shield showing a source or pressurized air connected thereto.

The face shield comprises a frame 1, a glass 2 attached to the frame, a padding 3 located between the frame and the face and a ribbon 4, which is tightened around the head. Air is led into the face shield through a hose 5. The frame 1 is hollow so that the air led into the face shield is directed into the hollow frame and the frame 1 comprises openings 6, through which the air is discharged into the face shield. The openings 6 are elongated slots located at the sides of the frame 1 and directed towards the glass so that the air is discharged in front of the face to be breathed and simultaneously to blow away possible mist from the inner surface of the glass. The padding 3 between the frame 1 and the face consists of a foam plastic with open cells so that the air, which has been led in to be breathed can together with the exhalation air exit through said padding from inside the face shield.

Especially in connection with a blowing device and also with compressed air a face shield of this type is needed, which is easy to use, light and not expensive. The padding does not necessarily have to be according to the example, it may also have closed cells or in some other way air impermeable, whereby the extra air is removed through a separate exit opening. In this case glass does not mean glass material but a transparent shield plate, which in reality is transparent plastic or so called plexiglass.

We claim:

1. A face shield comprising:
   a) a unitary frame comprising an enclosed, one-piece channel, the channel defining at least one opening therein;
   b) a shield plate connected to the frame;
   c) a padding connected to the interior surface of the frame;
   d) a ribbon connected to the frame and operable to secure the face shield to the head of a user;
   e) a source of pressurized air connected to the frame; and
   f) means for introducing pressurized air into the frame, whereby the pressurized air is introduced through the at least one opening in the channel into the interior of the face shield, and exhaled air is forced through the padding from the interior of the face shield to the outside environment.

2. The face shield of claim 1 wherein the at least one opening comprises an elongated slot.

3. The face shield of claim 1 wherein the at least one opening comprises a plurality of openings.

4. The face shield of claim 1 wherein the at least one opening in the channel is directed toward the shield plate so that the air introduced into the face shield is discharged in front of the face of the user to be breathed and to blow away mist from the inner surface of the shield plate.

5. The face shield of claim 1 wherein the means for introducing air into the frame comprises a hose.

6. The face shield of claim 1 wherein the padding is formed of foam plastic having open cells, the open cells operable to allow the air that is introduced into the face shield to exit the face shield through the padding.

7. The face shield of claim 1 wherein the padding is removable and replaceable.

8. The face shield of claim 1 wherein the padding may be sized to fit the face of a particular user.

9. A face shield comprising:
   a) a unitary frame comprising at least one air inlet and an enclosed, one-piece channel defining at least one opening therein;
   b) a source of pressurized air connected to the at least one air inlet;
   c) a shield plate connected to the frame;
   d) a ribbon connected to the frame and operable to secure the face shield to the head of a user; and
   e) an open-celled padding material connected to the frame and positioned to rest against the face of the user when the face shield is secured to the user, whereby the source of pressurized air forces air into the interior of the face shield through the air inlet, the channel and the at least one opening in the channel to be breathed by the user, and exhaled air and the excess pressurized air is forced through the open-celled padding material to exit the face shield.

10. The face shield of claim 9 wherein the at least one opening in the channel is directed toward the shield plate so that the air introduced into the face shield is discharged in front of the face of the user to be breathed and to blow away mist from the inner surface of the shield plate.

11. The face shield of claim 9 wherein the source of pressurized air is connected to the air inlet by a hose.

12. The face shield of claim 9 wherein the padding is removable and replaceable.

13. The face shield of claim 9 wherein the padding may be sized to fit the face of a particular user.

14. A face shield comprising:
   a) a unitary frame comprising at least one air inlet and an enclosed channel defining at least one opening therein, the frame being formed from a blow-molding process such that the enclosed channel is formed in one piece;
   b) a source of pressurized air connected to the at least one air inlet:
   c) a shield plate connected to the frame, the at least one opening in the channel directed toward the inner surface of the shield plate;
   d) a ribbon connected to the frame and operable to secure the face shield to the head of a user; and
   e) a removable, open-celled padding material connected to the frame and positioned to rest against the face of the user when the face shield is secured to the user, whereby the source of pressurized air forces pressurized air into the interior of the face shield through the air inlet, the channel and the at least one opening in the channel to be breathed by the user and to blow away mist from the inner surface of the shield plate, and exhaled air and the excess pressurized air is forced through the open-celled padding material to exit the face shield.

15. The face shield of claim 14 wherein the padding may be sized to fit the face of a particular user.

* * * * *